United States Patent
Gabriele et al.

(10) Patent No.: US 11,124,762 B2
(45) Date of Patent: Sep. 21, 2021

(54) PH-MODULATING BIODEGRADABLE POLYMER AND POLY(GLYCEROL SEBACATE)-AUGMENTED CELL CULTURE MEDIA

(71) Applicant: THE SECANT GROUP, LLC, Telford, PA (US)

(72) Inventors: Peter D. Gabriele, Frisco, TX (US); Jeremy J. Harris, Doylestown, PA (US); Charles Brendan Nicholson, Perkasie, PA (US); Steven Lu, Ambler, PA (US); Brian Ginn, Norristown, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 289 days.

(21) Appl. No.: 16/250,690

(22) Filed: Jan. 17, 2019

(65) Prior Publication Data
US 2019/0218506 A1   Jul. 18, 2019

Related U.S. Application Data

(60) Provisional application No. 62/624,566, filed on Jan. 31, 2018, provisional application No. 62/618,419, filed on Jan. 17, 2018.

(51) Int. Cl.
| | |
|---|---|
| *C12N 5/00* | (2006.01) |
| *A61L 27/18* | (2006.01) |
| *C08G 63/685* | (2006.01) |
| *C08K 5/17* | (2006.01) |
| *C08G 63/91* | (2006.01) |
| *A61L 27/50* | (2006.01) |
| *C08K 3/32* | (2006.01) |
| *C08K 3/26* | (2006.01) |
| *A61L 27/58* | (2006.01) |
| *C08L 67/00* | (2006.01) |
| *A61L 27/38* | (2006.01) |

(52) U.S. Cl.
CPC ............ *C12N 5/0018* (2013.01); *A61L 27/18* (2013.01); *A61L 27/38* (2013.01); *A61L 27/50* (2013.01); *A61L 27/58* (2013.01); *C08G 63/6854* (2013.01); *C08G 63/914* (2013.01); *C08K 3/26* (2013.01); *C08K 3/32* (2013.01); *C08K 5/175* (2013.01); *C08L 67/00* (2013.01); *C12N 2500/32* (2013.01); *C12N 2500/50* (2013.01)

(58) Field of Classification Search
CPC .......... C08L 67/00; C08L 89/00; A61L 27/18; A61L 27/38; A61L 27/50; A61L 27/58; C08K 3/26; C08K 3/32; C08K 5/175; C08G 63/6854; C08G 63/914; C12N 2500/32; C12N 2500/50; C12N 5/0018
See application file for complete search history.

(56) References Cited

U.S. PATENT DOCUMENTS

| | | | |
|---|---|---|---|
| 6,065,476 | A | 5/2000 | Agrawal et al. |
| 6,419,945 | B1 | 7/2002 | Gresser et al. |
| 7,722,894 | B2 | 5/2010 | Wang et al. |
| 9,359,472 | B2 | 6/2016 | Nicholson et al. |
| 2012/0143347 | A1 | 6/2012 | Wang et al. |
| 2013/0231412 | A1 | 9/2013 | Langer et al. |
| 2015/0322202 | A1 | 11/2015 | Wang et al. |
| 2017/0035932 | A1 | 2/2017 | Sant et al. |

FOREIGN PATENT DOCUMENTS

WO      2016057662 A1      4/2016

OTHER PUBLICATIONS

Ranjana Rai, et al. "Biomimetic poly(glycerol sebacate) (PGS) membranes for cardiac patch application", Materials Science and Engineering C, vol. 33, No. 7, May 4, 2013, pp. 3677-3687.
Yaobin Wu, et al. "Self-healing supramolecular bioelastomers with shape memory property as a multifunction platform for biomedical applications via modular assembly", Biomaterials, vol. 104, Jul. 9, 2016, pp. 18-31.
Marwa Tallawi, et al. "Poly(Glycerol Sebacate) Films Modified by Thermal Proteins for Cardiac Tissue Engineering", Proceedings of the IASTED International Conference on Biomedical Engineering, BioMed 2013, Feb. 13-15, 2013, pp. 485-490.
Zhengwei You, et al. "A functionalizable polyester with free hydroxyl groups and tunable physiochemical and biological properties", Biomaterials, vol. 31, No. 12, Feb. 9, 2010, pp. 3129-3138.
Pier Francesco Ferrari, et al. "Small Diameter Vascular Grafts Coated with Gelatin", Chemical Engineering Transactions, vol. 57, 2017, pp. 1441-1446.

*Primary Examiner* — Blaine Lankford
(74) *Attorney, Agent, or Firm* — McNees Wallace & Nurick LLC

(57) ABSTRACT

A pH-modulating poly(glycerol sebacate) composition includes poly(glycerol sebacate) and at least one pH-modulating agent associated with the poly(glycerol sebacate). A process of making a pH-modulating poly(glycerol sebacate) composition includes forming a poly(glycerol sebacate) by a water-mediated reaction from glycerol and sebacic acid and associating at least one pH-modulating agent with the poly(glycerol sebacate). A process of modulating a pH of a buffered aqueous solution includes placing a pH-modulating poly(glycerol sebacate) composition in a buffered aqueous solution. The pH-modulating agent is released into the buffered aqueous solution during degradation of the poly (glycerol sebacate) to reduce a decrease in pH of the buffered aqueous solution caused by degradation of the poly(glycerol sebacate).

7 Claims, 1 Drawing Sheet

PH-MODULATING BIODEGRADABLE POLYMER AND POLY(GLYCEROL SEBACATE)-AUGMENTED CELL CULTURE MEDIA

CROSS-REFERENCE TO RELATED APPLICATIONS

This application claims priority to and the benefit of U.S. Provisional Application No. 62/618,419 filed Jan. 17, 2018 and U.S. Provisional Application No. 62/624,566 filed Jan. 31, 2018, both of which are hereby incorporated by reference in their entirety.

FIELD OF THE INVENTION

The present application is generally directed to pH-modulating polymers and cell culture. More specifically, the present application is directed to processes of making poly (glycerol sebacate) (PGS) with pH-modulating characteristics, pH-modulating PGS compositions formed from such processes, articles of manufacture created from or with pH-modulating PGS, and the use of pH-modulating PGS for applications, such as cell culture, cell expansion, cell delivery, cell therapy, drug delivery applications, implantable medical devices and/or topical medical devices, and augmented cell culture media.

BACKGROUND OF THE INVENTION

Poly(glycerol sebacate) (PGS) is a cross-linkable elastomer formed as a co-polymer from glycerol and sebacic acid. PGS is biocompatible and biodegradable, reduces inflammation, improves healing, and has antimicrobial properties, all of which make it useful as a biomaterial in the biomedical field.

To utilize PGS for cell culture, PGS resin is cured to form thermoset scaffolds/substrates. However, culturing cells on PGS substrates remains a challenge. After curing, the PGS thermoset retains a portion of low molecular weight (LMW) fractions that can leach out into aqueous solutions, such as cell culture media. These LMW fractions are acidic and reduce the pH level of a physiological buffered solution into which they are released. In addition, degradation of the thermoset releases acidic degradation products over time. Since cultured cells typically grow best at pH levels of about 7.2 to about 7.4, a drop in pH may reduce cell growth, cell attachment, and/or cell viability.

To utilize PGS for medical device applications, modulation of wound/tissue pH is critical to the maintenance of the healing process. The various steps of the healing process, from the initial inflammatory response to the tissue remodeling phase, are all responsive to the wound pH and can vary from pH values of 5 to 8, depending on the stage of healing.

Conventional cell culture media come in a number of different forms, including solids, semi-solids, liquids, and gels. Two predominate compositions and uses of media designed to support microscopic life forms are for bacterial, viral, and fungal microorganisms and for stem cells, somatic cell, and some forms of plant life.

Media may be further classified as defined or undefined. Undefined media includes a carbon source, water, salts, and a complex of amino acids, nucleic acids, or other protein sources. Defined media has a well-defined composition where the elements of nutrition are known.

Media may be classified further as minimal, selective, differential, or transport.

Two-dimensional (2-D) Petri dish formats and liquid cell cultures are giving way to 3-D cell culture bioreactors, as it has been recognized that cells in vivo naturally develop in 3-D environments, but the materials used in these 3-D cell culture bioreactors may not fully or sufficiently mimic an in vivo environment.

BRIEF DESCRIPTION OF THE INVENTION

It would be desirable to have a biodegradable polymeric material that minimally alters the pH of a buffered aqueous solution into which the material degrades.

It would be desirable to have a medical device with a biodegradable polymeric film with the capacity to maintain would pH values required of the specific phase of the healing process.

It would also be desirable to improve cell culture viability, media compositions, bioreactor constructs for cell culture, and/or cell support, cell development, and/or cell storage related to somatic, stem, and/or microbiological cell therapeutics, blood storage, microbial culture, and/or tissue engineering.

In an embodiment, a pH-modulating poly(glycerol sebacate) composition includes poly(glycerol sebacate) and at least one pH-modulating agent associated with the poly (glycerol sebacate).

In another embodiment, a process of making a pH-modulating poly(glycerol sebacate) composition includes forming a poly(glycerol sebacate) by a water-mediated reaction from glycerol and sebacic acid and associating at least one pH-modulating agent with the poly(glycerol sebacate).

In yet another embodiment, a process of modulating a pH of a buffered aqueous solution includes placing a pH-modulating poly(glycerol sebacate) composition in a buffered aqueous solution. The pH-modulating poly(glycerol sebacate) composition includes poly(glycerol sebacate) and at least one pH-modulating agent associated with the poly (glycerol sebacate). The pH-modulating agent is released into the buffered aqueous solution during degradation of the poly(glycerol sebacate) to reduce a decrease in pH of the buffered aqueous solution caused by degradation of the poly(glycerol sebacate).

In another embodiment, a process of forming a pH-modulating poly(glycerol sebacate) resin includes charging a pH-modulating agent into glycerol, sebacic acid, and water in a reaction vessel. The process also includes heating the reaction vessel under a cool water reflux until the contents of the reaction vessel are molten. The process further includes distilling off the water under a nitrogen purge and maintaining the reaction vessel at about 120° C. to 130° C. for about 6 hours to 8 hours to form the pH-modulating poly(glycerol sebacate) resin. The pH-modulating agent is greater than 5% by weight of the pH-modulating poly (glycerol sebacate) resin.

In another embodiment, a cell culture medium includes an aqueous cell culture solution and a composition located in the aqueous cell culture solution. The composition includes a co-polymer and an augmentation agent contained by the co-polymer. The co-polymer is a poly(glycerol sebacate) or a poly(glycerol sebacate urethane).

In yet another embodiment, a method of culturing biological cells includes placing the biological cells in an augmented cell culture medium. The method also includes culturing the biological cells in the augmented cell culture medium under cell culture conditions.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

A pH-modulating poly(glycerol sebacate) (PGS) composition releases a pH-modulating agent into an aqueous solution during degradation of the PGS to reduce or mitigate a decrease in pH of the aqueous solution caused by degradation of the poly(glycerol sebacate).

A pH-modulating agent, as used herein, refers to any chemical compound that modulates the effect on pH of the base polymer composition as the base polymer composition degrades and releases degradation produces, including the pH-modulating agent, into a solution.

An augmented cell culture media improves cell culture viability, bioreactor constructs for cell culture, and/or cell support, cell development, and/or cell storage related to cell therapeutics, blood storage, microbial culture, and/or tissue engineering.

The pH-modulating PGS composition may take any of a number of different forms, including, but not limited to, a resin, a thermoset, a cast film, a coating, a microsphere, a microparticle, a scaffolding component, or a surface-functionalized scaffolding component.

In exemplary embodiments, PGS is modified with one or more pH-modulating agents to form a pH-modulating PGS composition. In some embodiments, the pH-modulating agent includes a weak base. In some embodiments, the pH-modulating agent includes a weak acid. In some embodiments, the pH-modulating agent includes an amino acid. The pH-modulating agent provides the PGS with pH-modulating characteristics. As the PGS releases acidic low molecular weight (LMW) fractions during degradation, the pH-modulating agent is also released into the surrounding media, thus attenuating a pH change. By preventing a significant pH change, the pH-modulating agent helps to maintain a predetermined pH in a medium for cell growth during degradation of the PGS.

A weak base, as used herein, refers to a chemical base that does not fully ionize in an aqueous solution.

A weak acid, as used herein, refers to a chemical acid that does not fully ionize in an aqueous solution.

Figure 1:
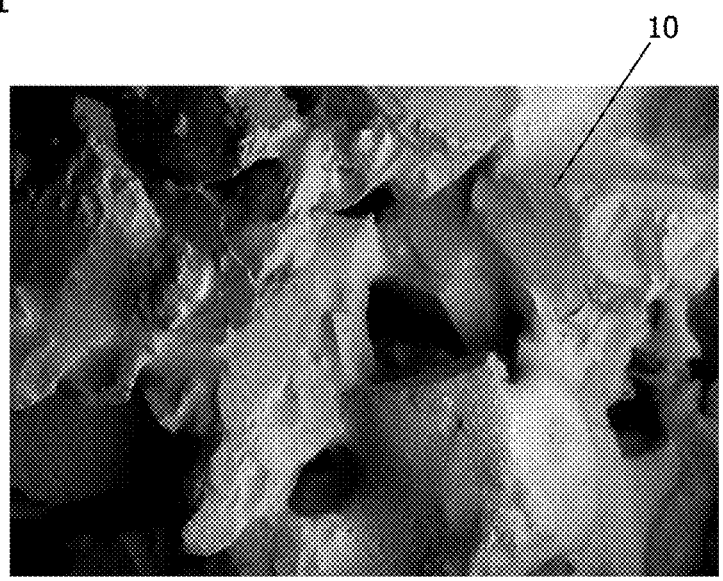
FIG. 1 shows a scaffold that in exemplary for a pH-modulating poly(glycerol sebacate) composition.

FIG. 1 shows a scaffold 10 that is exemplary for a pH-modulating poly(glycerol sebacate) composition.

In exemplary embodiments, pH-modulating agents are utilized to modify PGS to provide a PGS scaffold with pH-modulating characteristics. This allows the scaffold to maintain a predetermined pH range for cell growth and expansion. Depending on the predetermined pH range and the pKa of the pH-modulating agent, the pH-modulating PGS may also be self-buffering. A self-buffering system prolongs cell culture without the need for changing media, even as waste products from living cells or tissues are produced.

Appropriate agents for pH modulation may include, but are not limited to, inorganic salts, such as, for example, bicarbonate and phosphate dibasic, amino acids, such as, for example, arginine (Arg), histidine (His), lysine (Lys), and tyrosine (Tyr), proteins, such as, for example hemoglobin and metalloproteins, and citrates. Formula 1 schematically shows the structure of an amino acid-PGS conjugate:

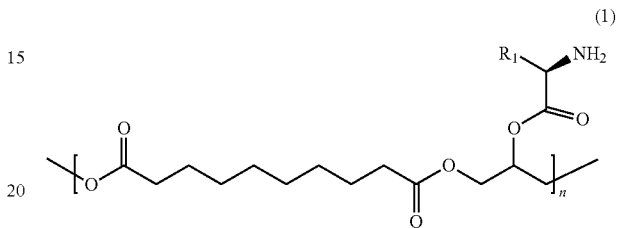

(1)

Additionally or alternatively, the modulation of the pH may be tuned to improve drug delivery. Certain drugs are pH-sensitive, and their uptake by cells is influenced by the isoelectric point of the drug and the pH of the surrounding medium. By tuning the PGS to maintain a certain predetermined pH range of the local environment, drug delivery and uptake may be enhanced or attenuated.

In exemplary embodiments, one or more pH-modulating agents, such as, for example, amino acids, are incorporated as pH-modulating agents to modulate the pH of the local environment or the solution during degradation of the PGS. Amino acids are amphoteric in nature, allowing them to maintain buffering capacity at different pHs, based on the pKas of the chosen amino acid. Depending on the amino acid used, a negative, positive, or neutral charge may be imparted to the PGS scaffold. In particular, a positive charge throughout the polymer or on the surface may improve cell adhesion and growth, as well as improve the uptake of drugs due to the negative charge of cell membranes. The amino acid may also change the hydrophilicity/hydrophobicity of the scaffold, which influences protein adsorption and conformation. The amount, type, and conformation of adsorbed proteins has a significant effect on cell attachment and growth. In addition, amino acids are essential nutrients to cells.

A pH-modulating PGS composition may be used to culture many different cell types, including, but not limited to, immortalized cell lines, primary cells, secondary cells, transfected and/or transdifferentiated cells, anchorage-independent (non-adherent) cells, and/or anchorage-dependent (adherent) cells.

In some embodiments, arginine, histidine, and/or lysine are selected as the pH-modulating agent to attenuate the pH drop in the surrounding medium due to PGS degradation. At a physiological pH of about 7.4, these three amino acids are weak bases and have a net positive charge.

To increase the hydrophilicity of the PGS, the PGS may be modified with aspartic acid, proline, glutamic acid, asparagine, lysine, arginine, glutamine, serine, and/or threonine.

The pH-modulating agent may be incorporated into the pH-modulating PGS by dispersing into the polymer matrix or by covalently incorporating into the PGS chemical structure. In exemplary embodiments, the pH-modulating agent is a crosslinker for the PGS. Due to the multifunctional nature of amino acids, they may act as a crosslinker and/or a chain extender for the pH-modulating PGS polymer.

Alternatively, the pH-modulating agent may be covalently reacted onto the surface of the thermoset PGS scaffold to provide one or more targeted surface characteristics, including, but not limited to, a predetermined hydrophilicity/hydrophobicity, a predetermined surface charge, and/or a predetermined surface functionality for further pH-modulating agent/amino acid/peptide attachment.

Although PGS scaffolds may be processed and treated to remove non-reacted and LMW fractions from the cured, crosslinked thermoset, the thermoset is still a degradable biomaterial that releases acidic degradation products over time. Additionally, even though a high media-to-PGS ratio may be used to maintain the overall physiologic pH of the cell culture medium, cells may still react to a drop in pH in the local environment of the PGS. Releasing pH-modulating agents from the pH-modulating PGS may maintain the local environment at a predetermined pH level beneficial for cell attachment, cell growth, and/or cell expansion.

The local pH environment may also or alternatively be modulated to maintain a pH level beneficial for drug intake into cells and tissues, regardless of the pH of the surrounding medium. For example, the pH-modulating agent may also control the pH and/or the charge of the degrading structure, such as a scaffold, which may also affect protein absorption and cell behavior at the surface.

The amount and the type of the pH-modulating agent may be selected to control the local environment for cell lines. Some cell lines may preferentially grow at different pH levels, such as an environment having a pH in the range of 7.2 to 7.4, a more acidic environment having a pH in the range of 7.0 to 7.2 or lower, or a more basic environment having a pH in the range of 7.4 to 7.7 or higher. The bulk pH of the solution, however, may not be the only factor determining cell growth. Polymeric surface charge may affect protein absorption, which affects cell attachment and growth. For example, the presence of lysine as a pH modulating agent changes the surface charge of the polymer, which promotes protein absorption, and was observed to aid in cell attachment and growth.

In exemplary embodiments, the PGS resin is formed by a water-mediated process, such as disclosed in U.S. Pat. No. 9,359,472, which is hereby incorporated by reference in its entirety.

In exemplary embodiments, glycerol is added to a reaction vessel with water under stirring. After dissolution of the glycerol, the sebacic acid is added to the reaction vessel. The amounts of the glycerol and the sebacic acid are selected to provide a predetermined molar ratio of free hydroxyl groups to free carboxyl groups in the range of 1:2 to 2:1, alternatively 1:1 to 2:1, alternatively 5:4 to 7:4, alternatively about 5:4, alternatively about 3:2, alternatively about 7:4, or any ratio, range, or sub-range therebetween. The reaction vessel is then fitted with a condenser to reflux water during the melt and stir steps of the polymerization, with the condenser temperature being set in the range of 1° C. to 10° C., 1° C. to 5° C., about 5° C., about 2.5° C., or any range, or sub-range therebetween. The reaction vessel is then heated to a mantle temperature in the range of 50° C. to 200° C., alternatively 100° C. to 180° C., alternatively 115° C. to 165° C., alternatively about 130° C., alternatively about 140° C., alternatively about 150° C., or any value, range, or sub-range therebetween, under stirring for a time in the range of 15 to 120 minutes, alternatively 30 to 120 minutes, alternatively 45 to 90 minutes, alternatively 60 to 80 minutes, alternatively about 60 minutes, alternatively about 70 minutes, alternatively about 80 minutes, or any value, range, or sub-range therebetween.

After the sebacic acid melts, the zone temperature is set to 50° C. to 200° C., alternatively 100° C. to 160° C., alternatively 120° C. to 140° C., alternatively about 120° C., alternatively about 130° C., alternatively about 140° C., or any value, range, or sub-range therebetween, and the mixture is stirred under reflux for 15 to 120 minutes, alternatively 30 to 90 minutes, alternatively 40 to 60 minutes, alternatively about 40 minutes, alternatively about 50 minutes, alternatively about 60 minutes, or any value, range, or sub-range therebetween.

The condenser is then removed, and the vessel is fitted with a distillation condenser to remove water from the vessel. A nitrogen purge is applied to the vessel and the zone temperature is set in the range of 50° C. to 200° C., alternatively 100° C. to 140° C., alternatively 110° C. to 130° C., alternatively about 110° C., alternatively about 120° C., alternatively about 130° C., or any value, range, or sub-range therebetween. During the distillation, the contents of the vessel are stirred at a temperature in the range of 50° C. to 200° C., alternatively 100° C. to 140° C., alternatively 110° C. to 130° C., alternatively about 110° C., alternatively about 120° C., alternatively about 130° C., or any value, range, or sub-range therebetween, for in the range of 1 to 48 hours, alternatively 6 to 36 hours, alternatively 12 to 36 hours, alternatively 20 to 28 hours, alternatively 22 to 26 hours, alternatively about 24 hours, or any value, range, or sub-range therebetween.

Next, a vacuum line is connected to the distillation condenser and a sub-atmospheric pressure is applied to the contents of the vessel. The pressure is reduced slowly and stepwise over 15 to 120 minutes, alternatively 30 to 120 minutes, alternatively 60 to 110 minutes, alternatively 75 to 95 minutes, alternatively about 75 minutes, alternatively about 85 minutes, alternatively about 95 minutes, or any value, range, or sub-range therebetween, to a target pressure of 30 Torr or less, alternatively 5 to 30 Torr, alternatively 20 Torr or less, alternatively 5 to 20 Torr, alternatively 10 to 20 Torr, alternatively about 15 Torr, alternatively about 20 Torr, alternatively about 25 Torr, or any value, range, or sub-range therebetween.

Once the pressure in the reaction vessel reaches the target pressure, the vacuum pump is set to a lower pressure of 20 Torr or less, alternatively 5 to 20 Torr, alternatively 10 Torr or less, alternatively 5 to 10 Torr, alternatively about 5 Torr, alternatively about 10 Torr, alternatively about 15 Torr, or any value, range, or sub-range therebetween. Following the application of vacuum, the reaction vessel is left to react for 1 to 48 hours, alternatively 6 to 36 hours, alternatively 12 to 36 hours, alternatively 22 to 30 hours, alternatively 24 to 28 hours, alternatively about 26 hours, or any value, range, or sub-range therebetween, at a temperature in the range of 50° C. to 200° C., alternatively 100° C. to 160° C., alternatively 120° C. to 140° C., alternatively about 120° C., alternatively about 130° C., alternatively about 140° C., or any value, range, or sub-range therebetween, under stirring, with the sub-atmospheric pressure set to the lower pressure.

Next, the product in the reaction vessel is transferred to a glass jar and allowed to cool on the bench top for 15 to 120 minutes, alternatively 30 to 90 minutes, alternatively 35 to 55 minutes, alternatively about 35 minutes, alternatively about 45 minutes, alternatively about 55 minutes, or any value, range, or sub-range therebetween, then is transferred to a freezer for storage, where it is frozen for at least 12 hours, alternatively at least 18 hours, alternatively at least about 24 hours, or alternatively at least 48 hours.

In exemplary embodiments, the PGS resin is thermoset by heating to and maintaining at a temperature in the range of 110° C. to 140° C., such as, for example, about 130° C., and a reduced pressure of about 10 Torr for a period of time in the range of 8 hours to 168 hours, such as, for example, about 24 hours. The resultant thermosets are suitably cohesive and tack-free. In some embodiments, the thermosets are formed as thin films having a thickness of about 2 mm or less, alternatively about 1 mm or less, alternatively 0.5 mm to 1.5 mm, alternatively about 1 mm, or any value, range, or sub-range therebetween. In some embodiments, the molten PGS resin is poured into a round aluminum dish to form the shape of the thin film.

For certain pH-modulating agents, the pH-modulating agent may be provided prior to polymerization. In an exemplary embodiment, the pH-modulating agent is charged into glycerol and sebacic acid and deionized water in a reaction vessel. The materials in the vessel are heated to about 120° C. to 130° C. under cool water reflux. Once all material are molten, the water is distilled off of the mixture under a nitrogen purge flowing at about 5-15 L/min. Once the water is removed, which may take about 30-60 minutes, the reactor temperature is maintained at about 120° C. to 130° C. for about 24 hours. Following this, the temperature is increased to about 130° C. and the pressure is reduced to about 5-15 Torr for at least 24 hours.

In another exemplary embodiment, the pH-modulating agent is charged into glycerol and sebacic acid and deionized water in a reaction vessel. The materials in the vessel are heated to about 120° C. to 130° C. under cool water reflux. Once all material is molten, the water is distilled off of the mixture under a nitrogen purge flowing at about 5-15 L/min. Once the water is removed, which may take about 30-60 minutes, the reactor temperature is maintained at about 120° C. to 130° C. for about 8 hours or less, alternatively about 6 hours, or any value, range, or sub-range therebetween, to form a resin. The resin is thermoset by heating to and maintaining the composition at about 115-125° C. for about 8 hours or less under a reduced pressure of about 5-15 Torr to form the thermoset.

Depending on the desired result, the pH-modulating agent may be incorporated into PGS at any of a number of different points in the synthesis of the PGS reaction or before, during, or after formation of the thermoset, including, but not limited to, at the beginning of the reaction, after the nitrogen purge step, after the vacuum step, admixed with the resin before thermosetting, and after thermosetting, such as to modify or functionalize the surface of the thermoset. The pH-modulating agent may also be loaded into PGS by any of various drug loading methods, which may include, but are not limited to, shear mixing and a swell method.

The pH-modulating agent may be combined with or included in PGS in any appropriate amount, by weight with respect to the weight of the pH-modulating PGS composition, such as, for example, about 10% or less, 1% to 10%, 2% to 8%, 4% to 6%, 1% to 5%, 2% to 5%, about 4%, about 5%, about 6%, about 5% or greater, 5% to 10%, 8% to 12%, about 8%, about 9%, about 10%, about 10% or greater, about 11%, about 12%, 10% to 12%, 10% to 15%, or any value, range, or sub-range therebetween. Since the presence of the pH-modulating agent may both increasingly affect the level of pH-modulation and increasingly alter the physical properties of the polymer with increasing amounts of the pH-modulating agent, both of those effects may be taken into consideration when selecting the amount of pH-modulating agent in the PGS for a particular application. At higher levels of the pH-modulating agent, however, the pH-modulating agent may behave as a physical filler, which may have additional benefits.

In some embodiments, the processing conditions for forming the PGS resin may be adjusted based on the incorporation of the pH-modulating agent. For example, when lysine was incorporated at 10% by weight into the PGS, the resin processing time was surprisingly reduced from about 24 hours or greater to about 8 hours or less and occurred without a pressure reduction. Additionally, the thermosetting time was reduced from about 24 hours to about 8 hours and the thermosetting temperature was reduced from about 130° C. to about 120° C. with lysine at 10%. Thus, the incorporation of lysine or other pH-modulating agents in amounts of more than 5% by weight may further have the effect of providing a method of forming a PGS resin that reduces manufacturing time by as much as 75% or more.

It will further be appreciated that synthesis of highly crosslinked PGS-based materials (e.g. poly(glycerol sebacate urethane) (PGSU)) may include the use of isocyanates or other non-biologically friendly crosslinking agents, which may be undesirable in certain biological environments, such as implants, because of concerns of isocyanate release upon degradation of the PGSU within the body. The use of amino acids as the pH modulator provides an additional advantage in that it acts as a biological-friendly crosslinking agent with the replacement of the isocyanate with an amino acid. This incorporation alleviates the risk of a cytotoxic response due to the releases of the isocyanate moiety during degradation. The incorporation of an amino acid provides a pH-modulating, cell friendly, highly crosslinked PGS composition.

In some embodiments, the PGS and the pH-modulating agent are released into a surrounding augmented cell culture media that also includes an enhancement composition including a PGS (or a PGSU) containing composition. The enhancement composition further includes an augmentation agent.

In embodiments for cell culture media, an enhancement composition includes a nutrient-containing or functionally-modified form of PGS. In some embodiments, the enhancement composition includes a nutrient-containing or functionally-modified PGS (NPGS). In some embodiments, the enhancement composition includes a nutrient-containing or functionally-modified PGSU (NPGSU). The cell culture compositions disclosed herein may relate to any and all forms of cell culture media. In some embodiments, the enhancement composition may be part of an "instant" media single-use device characterized by just adding water to provide nutrient support that originates from the enhancement composition. The nutrition may be in the form of "dehydrated" compositions, where an enhancement composition coating converts to media support or media compositions.

A composition includes a biofriendly polymer and an augmentation agent contained by, or otherwise associated with, the biofriendly polymer. The composition is preferably in a solid or substantially solid state and is free or substantially free of solvent. In some embodiments, the composition is used in an augmented cell culture medium.

The augmentation agent may include, but is not limited to, a cell nutrient; a 2-3-diphosphoglycerate scavenger; a composition protecting against hemoglobin scavenging of nitrous oxide such as, for example, a stabilized hemoglobin protease, heme lipase, heme metalloprotease, or amino peptidases specific for hemoglobin; an affinity composition for toxins such as, for example, chelating agents or charged chemistries such as, for example, zwitterion entities; a fiber extrudate having specific enzymatic activity for hemoglobin; a paramagnetic material such as, for example, super paramagnetic iron oxide and other paramagnetic metals; a lactic acid scavenger through lactate dehydrogenase denaturation and other mechanisms to preserve aerobic respiration in storage including confined $O_2$ within polymer matrices including microparticles containing calcium peroxide and sodium percarbonate and other $O_2$-releasing oxides that may be bound to the film surface, incorporated by way of microparticle dispersion within the matrix, or dispersed within the polymer, the idea being that available $O_2$ within the storage containment avoids anaerobic pathways leading to lactic acid production; a cell preservation composition such as, for example, citric acid and citric acid compositions with amino acids such as, for example, arginine, adenosine, and adenine; an anti-coagulation composition such as, for example, citric acid, phosphate, dextrose, and adenine (CPDA); a sanitation composition such as, for example, a biocide, an antibiotic, or a biostatic compound; a surface passivation composition that mitigates pH shifting or reduces surface energy to minimize cell attachment to sidewalls; or combinations thereof.

In exemplary embodiments, compositions improve cell culture viability, media, bioreactor constructs for cell culture, and/or cell support, cell development, and/or cell storage related to cell therapeutics (such as, for example, somatic cells, stem cells, or microbiological cells), blood storage, microbial culture, and/or tissue engineering.

In some embodiments, a composition of a bulk combination of PGS and/or PGSU improves structural and engineering components, providing one or more of a plurality of nutrient, protective, preservation, and supporting benefits, which may include, but are not limited to, simple structural support of growth media including additives such as for preservation, anti-coagulation, sanitation, and improved shelf-live in biocontainment structures; material construction of bioreactor interior walls; modification to film compositions and composite containment wall design; scaffold structural support of cells during growth, regeneration, expansion, and preservation; solid, semi-solid, or gel vehicle-resin-polymer supporting nutrient components in the form of "coatings", adhesives, extrudates, implantable or transplantable tissue, or cell culture devices; modified polymers, resins, and vehicles for film coating, rigid, flexible planar (film) extrusion, or composite assemblies; biodegradable, self-cleaning, erodible nutrient support to prevent cell adhesion or attachment to reactor wall surfaces and particle devices; or combinations thereof.

The NPGS or NPGSU may be in the form of or form part of a composition of matter, a film, or an extruded structure. Additionally or alternatively, the NPGS or NPGSU is provided in methods of cell culture support in bioreactors or other devices supporting cell and tissue expansion and regeneration. The embodiments disclosed herein may be useful with both defined and undefined media.

Without wishing to be bound by theory, it is believed that PGS may augment cell culture response through support matrices for cell and tissue support. Unlike the agar that is conventionally used as a support media in microbiology, PGS is biodegradable and its monomeric components include the metabolites glycerol and sebacic acid that are known to support the Krebs cycle production of adenosine triphosphate (ATP) for cellular bioenergetic. This makes PGS a unique support material and polymer for constructs, in particular for eukaryotic somatic and stem cell expansion and differentiation. In addition, PGS is a surface degrader rather than a bulk degrader, making it a unique material for zero order delivery of nutrients. The benefits of PGS as a polymeric biodegradable matrix may include providing a matrix that is in support of metabolism of the developing cells. Likewise, a fortification of nutrient components to the PGS matrix is believed to improve cell support. In one embodiment, providing additional components of cell support via the PGS matrix increases the efficiency of bioenergetics related to cell culture expansion. Advantages of PGS as a culture medium and as a support medium include that PGS is inherently antimicrobial, is not immunogenic, is non-cytotoxic, is hemocompatible, and is antithrombic. PGS is also believed to be angiogenic, which may be beneficial for implant designs.

In bioreactor designs, PGS and co-polymers of PGS and PGSU extrudates, as well as PGS- and PGSU-anchored systems, may improve bioreactor interior wall efficiency by contributing to film and/or surface topography modification, incubation physiology, nutrition, protection, and combinations thereof; film functionality transformation for anti-adhesion of surface coatings; new materials of construction for film resins with respect to glycerol-ester polymer compounding; and new materials of construction for films and coating vehicles with respect to films for new polymer synthesis.

A PGS-based support medium may include any of a number of potential advantages. Where culture beads are used to support dimensional growth, cells often agglomerate and adhere to the beads, making it difficult to expand and harvest cells. Beads or PGS microspheres capable of surface erosion may be manufactured with various degrees of degradation rates, providing a surface that naturally sluffs expanded cells into the surrounding fluid. Likewise, standard bead technology may be coated with PGS to provide the surface erosion. In bioreactors, interior walls may be designed to self-clean by surface erosion, thereby preventing cell adhesion.

In one embodiment, PGS is formulated into a hydrogel, making PGS a preferred biodegradable polymer that provides excellent matrix support for 3-D cell culture. Here too, the benefit of a degradable and nutrient-providing support allows expanding cells that naturally configure into 3-D conformations to expand unrestricted as the biomass increases.

In another embodiment, PGS as a solid matrix fortified with either defined or undefined media may provide an enhanced scaffold structure support and encourage tissue growth and differentiation through temporal nutritional bioenergetic and trophic support. This may be particularly advantageous in cases where the scaffold structure is designed to provide a gradient for transitioning composite nutrient "layers" or films in the composition, as subsequent layers of domains are exposed through biodegradation or erosion, the concept being that early stage expansion or growth requires a different composition of nutrition than mature cells. This concept may be used to initiate differentiation within the growth cycle by supplying a trophic agent from independent temporally designed layers. The water-mediated process further provides for the incorporation of nutrients to be either entrapped or anchored into the polymer matrix or backbone, thereby a creating customized nutritional delivery.

In yet another embodiment, PGS is fashioned into a biodegradable nutrient coating, a film, a fiber, or a semi-rigid sheet. Combining the nutritional delivery embodiments described above, a PGS coating may be applied to any preferred polymeric film surface to be converted into a disposable bioreactor. Such a film provides biocompatibility, as well as nutrient support of the reactor walls and prevention of cell adhesion to reactor surfaces. Solid PGS nutrient films may be laid into polymeric films, creating a composite having a nutrient-containing biodegradable surface and a backside non-degradable engineering surface. Such a construction may be used to create a plurality of containment structures, including, but not limited to, a disposable bioreactor. Additionally, a nutrient coating may be useful as a passivation or growth enhancement coating or adhesive in surgical structures for implant.

In contrast to agar support media, NPGS offers versatility as a culture medium delivery platform, providing a more "realistic" 3-D environment for cell expansion in its solid and semi-solid form and providing temporal release of nutrient and trophic components from it both as a coating and as an engineered laminate, allowing almost any volumetric space the ability to be converted into a bioreactor. Potential PGS and PGSU features and benefits may include, but are not limited to, biodegradability by eukaryotic and antagonistic to prokaryotic cells; being formed of metabolic monomers accessible to the metabolizing organism by hydrolytic or enzymatic means; stoichiometric modification of the polymer to engineer an indigenous pH and/or hydrophilic environment; reactability with certain defined media components for incorporation into the polymer matrix; the ability to be engineered to have a temporal period of desired degradation and growth factor release; potential non-immunogenicity; and the ability to permit cells like RBCs to continue to metabolize in storage and often revert to anaerobic respiration as $O_2$ is depleted from an enclosed containment vessel. Lactic acid is a toxic by-product of anaerobic metabolism. Consequently, lactide and glycolide degradable resins may aggravate the toxic build-up. PGS and PGSU may be formulated with $O_2$-releasing compounds to prevent $O_2$ depletion and lactic acid build-up, as well as contributing glycerol and sebacic acid as metabolites in storage.

Certain embodiments hereof may be considered a "solid-state" nutrient or protective composition for a plurality of surfaces, including bioreactors and prosthetic devices where proliferation is an advantage to the regenerative or healing process.

In one embodiment, it is particularly economically advantageous to use NPGS where water is not transported or required for storage. NPGS also eliminates the need for cold storage for many defined media. NPGS may also provide for a conformal application of media to various surfaces and topologies otherwise limited by aqueous bulk compositions.

In addition to coated surfaces, microspheres including PGS or PGSU and adducts or anchored components may be useful to expansion.

A predominate use of NPGS may be for the support of cell expansion for cell therapy. However, such improvements provided by the polymer as a support matrix may have significant impact on both in vivo and ex vivo tissue engineering and growth-specific structural design.

There are many types of commercial media available, too many, too complex, and including too specialized materials to list. In one embodiment, a composition of matter is developed from a nutrient or functional modification and PGS or PGSU by blending, mixing, reacting in, compounding, coextruding, solvent blending, or other such methods of liquid-solid incorporation.

Compositions may be further modified with additional materials, including known materials, to control solid support, rheology, and compatibility as needed.

Material compositions may be further processed by lyophilization or dehydration to create non-liquid dry compositions for subsequent reconstitution.

In the form of a coating, the predominate mechanism of action may be surface erosion to release components into the growth chamber or biological space.

In the form of a film of variable crosslink density, the composition may be used as a material of construction for engineered constructs, whereby the interior surface exposed to an aqueous volume containing cells temporally erodes.

Aqueous-based culture media may lack bulk vehicle properties that may permanently conform and hold to a surface. In one embodiment, the incorporation of PGS as NPGS offers new use of volumetric surfaces.

In one embodiment, oxygen-releasing metal oxides and peroxides are included to provide oxygen support to avoid necrosis.

In addition to changing the stoichiometry of the glycerol:sebacic acid, NPGS may be synthesized with excess glycerol to increase the concentration of low-MW fractions of NPGS that are water-soluble. Low-MW fractions of NPGS are known to be soluble in aqueous solutions. As a soluble fraction, NPGS is more readily available to cells and tissues as a nutrient and/or supplement. In some embodiments, the molar ratio of glycerol:sebacic acid is in the range of 2:1 to 10:1. In another embodiment, the molar ratio of glycerol:sebacic acid is greater than 10:1.

In one embodiment, the NPGS may be applied to cancer therapy. Cancer cells are known to be hypoxic and have diminished energetics as compared to normal cells. It is further known that cancer metastases begin to form as the tumor, at a critical mass, produces interleukin (IL)-6 and IL-8. PGS breakdown products have been shown to "energize" cells. Aspirin is known to block IL-6 and IL-8. In some embodiments, a NPGS includes polyaspirin to form an injectable cell therapy and chemotherapeutic agent for solid tumors.

EXAMPLES

The invention is further described in the context of the following examples, which are presented by way of illustration, not of limitation.

Example 1

Four separate pH-modulating PGS resins were produced by charging 5.0±0.1 g of His, Lys, Arg, or Tyr into 95±1 g of Regenerez® PGS resin (The Secant Group, LLC, Telford, Pa.) and about 20 mL of deionized water (diH$_2$O) in a 500-mL reaction vessel. The materials in the vessel were heated to 120° C. under cool water reflux, then once all material was molten, the water was distilled off of the mixture under a nitrogen purge flowing at about 10 L/min. Once the water was removed, which took about 30 minutes, the reactor temperature was maintained at 120° C., and the pressure was reduced to 10 Torr. The remaining material was polymerized as such for about 4 hours then drained from the reactor. The resulting pH-modulating PGS resins, PGS-His (5%) resin, PGS-Lys (5%) resin, PGS-Arg (5%) resin, and PGS-Tyr (5%) resin, were then thermoset and/or characterized.

Example 2

Additionally, the incorporation of His at 5%, Lys at 5% and 10%, Arg at 5%, and Tyr at 5% into PGS resins was attempted during PGS resin synthesis. Of the amino acids attempted, only lysine was sufficiently soluble under the PGS reaction conditions and favorably incorporated into the PGS resin in this manner. When the amino acid was added to the reaction prior to the nitrogen step, the amino acid amounts were calculated from the expected stoichiometric yield of PGS resin at the average acid value for oligomeric (glycerol sebacate) (OGS) and PGS resins.

The PGS-Lys (5%) resin was produced by charging 10.0±0.1 g of Lys into 59.4±0.1 g of glycerol and 130.6±0.1 g of sebacic acid and about 40 mL of deionized water (diH$_2$O) in a 500-mL reaction vessel. The materials in the vessel were heated to about 120° C. under cool water reflux. Once all material was molten, the water was distilled off of the mixture under a nitrogen purge flowing at about 10 L/min. Once the water was removed, which took about 45 minutes, the reactor temperature was maintained at about 120° C. for about 24 hours. Following this, the temperature was increased to about 130° C. and the pressure was reduced to about 10 Torr for about 26 hours.

The PGS-Lys (10%) resin was produced by charging 20.0±0.1 g of Lys into 56.3±0.1 g of glycerol and 123.7±0.1 g of sebacic acid and about 40 mL of deionized water (diH$_2$O) in a 500-mL reaction vessel. The materials in the vessel were heated to about 120° C. under cool water reflux. Once all material was molten, the water was distilled off of the mixture under a nitrogen purge flowing at about 10 L/min. Once the water was removed, which took about 45 minutes, the reactor temperature was maintained at about 120° C. for about 6 hours. The resulting resin had a viscosity similar to PGS resins synthesized for greater than 50 hours.

Example 3

Portions of each of the 5% pH-modulating PGS resins from Example 1 were thermoset as films of approximately a 1-mm thickness by pouring each molten pH-modulating PGS resin into a round aluminum dish, then heating to and maintaining the polymer at 130° C. and a reduced pressure of 10 Torr for 24 hours. The resultant films, PGS-His (5%) thermoset, PGS-Lys (5%) thermoset, PGS-Arg (5%) thermoset, and PGS-Tyr (5%) thermoset, were suitably cohesive and tack-free.

Surprisingly, the PGS-Lys (10%) resin from Example 2 was thermoset by heating to and maintaining the polymer at 120° C. for only 8 hours under a reduced pressure of 10 Torr, a significant reduction in time and a significant advantage for large-scale manufacture of the pH-modulating thermoset. The PGS-Lys (10%) thermoset was suitably cohesive and tack-free.

Example 4

Round disks of pH-modulating PGS thermoset films were prepared by using a 1-mm inner diameter hole punch to cut samples from the films of Example 3. These disks were placed into separate wells of a 24-well plate and each disk was exposed to a 2.4 mL solution of about 0.01 M phosphate-buffered saline (PBS) having a pH of about 7.4 and stored in an incubator at a temperature of 37° C. for various time points. The pH of the PBS solution was tested daily for seven days.

Figure 2:
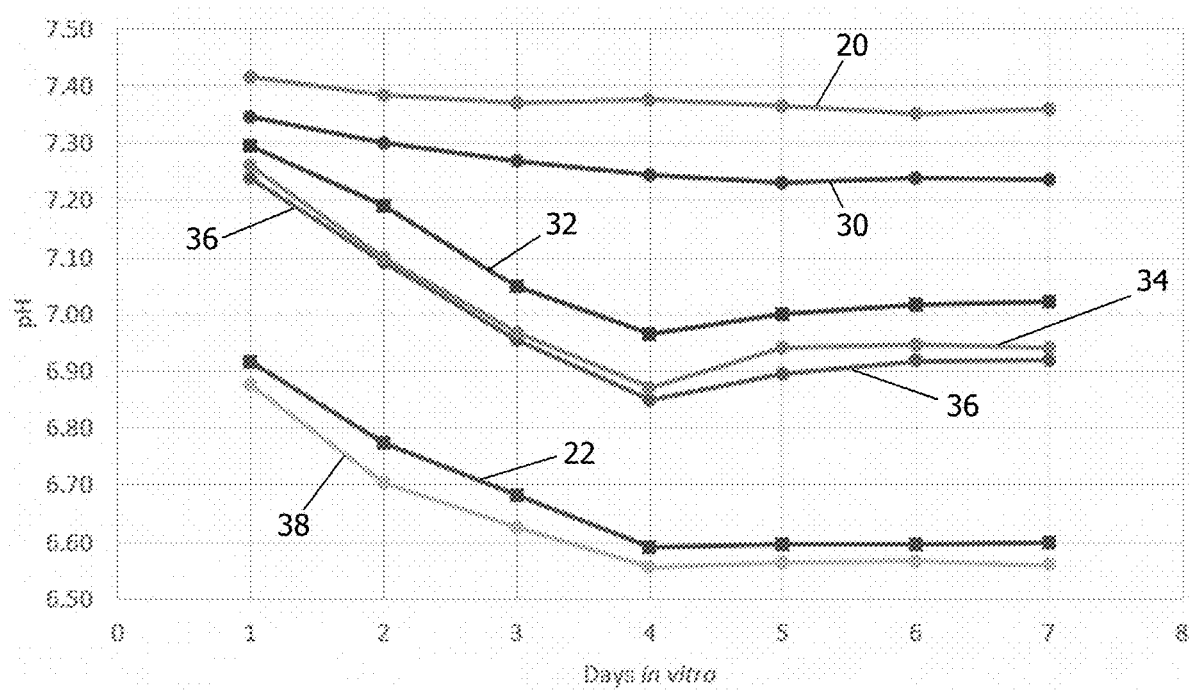
FIG. 2 shows a graph of the pH of PBS in the presence or absence of various pH-modulating compositions.

Referring to FIG. 2, a PBS blank 20 was included as a positive control, and a thermoset PGS 22 was included as a negative control. The test results show that most of the pH-modulating PGS thermosets mitigated the pH drop (higher resulting pH) relative to the standard PGS thermosets. As shown in FIG. 2, the pH of the PBS blank 20 is essentially unchanged from the initial pH of about 7.4 over the seven days monitored. In the absence of a pH-modulating agent, degradation of the thermoset PGS 22 lowers the pH of the PBS by about 0.5 to a value of 6.9 by Day 1 and by about 0.8 to a value of 6.6 by Day 4, where it remains through Day 7. The pH-modulating PGS thermosets showed a range of pH-modulating abilities from high to low of PGS-Lys (10%) 30, PGS-His (5%) 32, PGS-Arg (5%) 34, PGS-Tyr (5%) 36, and PGS-Lys (5%) 38, While the PGS-Lys (5%) 38 produced similar pH drops to the thermoset PGS control 22, PGS-His (5%) 32, PGS-Arg (5%) 34, and PGS-Tyr (5%) 36 each demonstrated significant pH modulation of the PBS. The drop in pH for PGS-His 32 was only about 0.10 at Day 1 and about 0.41 by Day 4. The drop in pH for PGS-Arg 34 was about 0.14 at Day 1 and about 0.53 by Day 4. The drop in pH for PGS-Tyr 36 was about 0.16 at Day 1 and 0.55 by Day 4. For all of the thermosets, the pH values plateaued or increased slightly from Day 4 through Day 7.

Lysine, being an outlier for pH-modulating at 5% loading, was also prepared at 10% loading. As shown in FIG. 2, by increasing the loading of lysine to 10%, the thermoset PGS-Lys surprisingly went from being the worst pH modulator to the best pH modulator. Without wishing to be bound by theory, it is believed that different extents of crosslinking by the amino acids lead to differences in their ability modulate the pH during degradation of the polymer.

Although pH modulation by amino acids has been described herein primarily with respect to PGS in PBS, amino acids or other pH-modulating agents may be similarly used to modulate the pH in other buffer systems and with other degradable polymers.

Other appropriate degradable polymers may include, but are not limited to, a diacid/polyol co-polymer, a PGS-lactic acid co-polymer, a polyester, a citrate-based polymer, a polycitrate, or a citrate/polyol co-polymer.

Other appropriate buffer systems may include, but are not limited to, organic buffers or cell culture media buffers, including, but not limited to, N-(2-Acetamido)-2-aminoethanesulfonic acid (ACES) buffer, N-(2-acetamido)iminodiacetic acid (ADA) buffer, 2-amino-2-methyl-1-propanol (AMP) buffer, 2-amino-2-methyl-1,3-propanediol (AMPD) buffer, 1,1-dimethyl-2-hydroxyethyl)amino)-2-hydroxypropanesulfonic acid (AMPSO) buffer, N,N-bis[2-hydroxyethyl]-2-aminoethanesulfonic acid (BES) buffer, Bicine buffer, 4-(cyclohexylamino)-1-butanesulfonic acid (CABS) buffer, N-cyclohexyl-3-aminopropanesulfonic acid (CAPS) buffer, 3-(cyclohexylamino)-2-hydroxy-1-propanesulfonic acid (CAPSO) buffer, N-cyclohexyl-2-aminoethanesulfonic acid (CHES) buffer, 3-(N,N-Bis[2-hydroxyethyl]amino)-2-hydroxypropanesulfonic acid, N,N-bis(2-hydroxyethyl)-3-amino-2-hydroxypropanesulfonic acid (DIPSO) buffer, 4-(2-hydroxyethyl)-1-piperazinepropanesulfonic acid, 4-(2-hydroxyethyl)piperazine-1-propanesulfonic acid, N-(2-hydroxyethyl)piperazine-N'-(3-propanesulfonic acid) (EPPS) buffer, Gly-Gly buffer, N-(2-hydroxyethyl)piperazine-N'-(4-butanesulfonic acid) (HEPBS) buffer, 4-(2-hydroxyethyl)-1-piperazineethanesulfonic acid (HEPES) buffer, 4-(2-hydroxyethyl)piperazine-1-(2-hydroxypropanesulfonic acid) (HEPPSO) buffer, sulfate buffers, 2-(N-morpholino)ethanesulfonic acid (MES) buffer, MOBS buffer, 3-morpholinopropane-1-sulfonic acid (MOPS) buffer, β-Hydroxy-4-morpholinepropanesulfonic acid (MOPSO) buffer, piperazine-N,N'-bis(2-ethanesulfonic acid) (PIPES) buffer, piperazine-N,N'-bis(2-hydroxypropanesulfonic acid) (POPSO) buffer, N-tris(hydroxymethyl)methyl-4-aminobutanesulfonic acid (TABS) buffer, [tris(hydroxymethyl)methylamino]propanesulfonic acid (TAPS) buffer, 3-[N-tris(hydroxymethyl)methylamino]-2-hydroxypropanesulfonic acid (TAPSO) buffer, triethanolamine (TEA) buffer, N-[tris(hydroxymethyl)methyl]-2-aminoethanesulfonic acid (TES) buffer, Tricine buffer, Tris(hydroxymethyl) aminomethane (Tris) buffer, Bis-Tris buffer, Bis-Tris Propane buffer, or Trizma buffer.

While the invention has been described with reference to one or more exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A process of modulating a pH of a buffered aqueous solution, the process comprising placing a pH-modulating poly(glycerol sebacate) composition in a buffered aqueous solution, the pH-modulating poly(glycerol sebacate) composition comprising poly(glycerol sebacate) and at least one pH-modulating agent associated with the poly(glycerol sebacate), the pH-modulating agent being released into the buffered aqueous solution during degradation of the poly(glycerol sebacate) to reduce a decrease in pH of the buffered aqueous solution caused by degradation of the poly(glycerol sebacate).

2. The process of claim 1, wherein the buffered aqueous solution has a pH in the range of 7.0 to 7.7 prior to placing the pH-modulating poly(glycerol sebacate) composition in the buffered aqueous solution.

3. The process of claim 1, wherein the at least one pH-modulating agent is selected from the group consisting of an inorganic salt, an amino acid, and a protein.

4. The process of claim 1, wherein the at least one pH-modulating agent is selected from the group consisting of arginine, histidine, and tyrosine.

5. The process of claim 1, wherein the at least one pH-modulating agent is lysine.

6. The process of claim 1, wherein the at least one pH-modulating agent is present in the pH-modulating poly(glycerol sebacate) composition in an amount, by weight, of about 5% or greater with respect to the weight of the pH-modulating poly(glycerol sebacate) composition.

7. The process of claim 1, wherein the at least one pH-modulating agent is present in the pH-modulating poly(glycerol sebacate) composition in an amount, by weight, of about 10% or greater with respect to the weight of the pH-modulating poly(glycerol sebacate) composition.

* * * * *